United States Patent [19]
Hazra et al.

[11] Patent Number: 6,090,952
[45] Date of Patent: Jul. 18, 2000

[54] (2R, 3S, 22R, 23R)-2,3,22,23-TETRAHYDROXY-24-ETHYL-β-HOMO-7-OXA-5α-CHOLESTAN-6-ONE AND A PROCESS FOR PREPARING THE SAME

[75] Inventors: Braja Gopal Hazra; Padmakar Laxman Joshi; Tirunahari Pavan Kumar, all of Maharashtra, India

[73] Assignee: Council of Scientific & Industrial Research, New Delhi, India

[21] Appl. No.: 09/050,180

[22] Filed: Mar. 30, 1998

[51] Int. Cl.[7] .................................................. C07D 313/06
[52] U.S. Cl. .................................................................... 549/268
[58] Field of Search ............................................... 549/268

[56] References Cited

PUBLICATIONS

Nobuo Ikekawa et al., *Chem. Pharm. Bull.* 1982, 30, 4181–4185.

Kenji Mori et al., *Tetrahedron* 1982, 38, 2099–2109.

C.W. Shoppe et al., *J. Chem. Soc.* 1957, 3100–3107.

B.G. Hazra et al.., *J. Chem. Soc.* Perkin Trans. I, 1994, 1667–1669.

*Primary Examiner*—Ba K. Trinh
*Attorney, Agent, or Firm*—Greenblum & Bernstein, P.L.C.

[57] ABSTRACT

The invention discloses a process for the preparation of a compound, having molecular formula $C_{29} H_{50} O_6$ and isomeric structural formulae (2R, 3S, 22R, 23R) −2, 3, 22, 23 -tetrahydroxy-24- ethyl-β-homo-7-oxa -5α- cholestan-6-one and (2R, 3S, 22S, 23S) −2, 3, 22-23-tetrahydroxy-24-ethyl-β-homo-7-oxa-5α-cholestan -6- one in a ratio 69:31, both of which are members of a new class of steroidal phytohormones.

8 Claims, 2 Drawing Sheets

FORMULA 1

FORMULA 2

FORMULA 3

FORMULA 4

FORMULA 5

FORMULA 6

FORMULA 7

FORMULA 8

FORMULA 9

FORMULA 10

FORMULA 11

FORMULA 12

(2R, 3S, 22R, 23R)-2,3,22,23-TETRAHYDROXY-24-ETHYL-β-HOMO-7-OXA-5α-CHOLESTAN-6-ONE AND A PROCESS FOR PREPARING THE SAME

FIELD OF THE INVENTION

This invention relates to process for the preparation of a compound having molecular formula $C_{29}H_{50}O_6$ and isomeric structural formulae (2R, 3S, 22R, 23R)-2, 3, 22, 23-tetrahydroxy -24-ethyl-β-homo-7-oxa-5α-cholestan-6-one which is shown as formula 8 in the accompanying drawings and (2R, 3S, 22s, 23s)-2,3,22-23-tetrahydroxy-24-ethyl-β-homo-7-oxa-5α-cholestan-6-one which is shown as formula 9 in the accompanying drawings. Compounds of the formulae 8 and 9 are important members of a new class of steroidal phytohormones. They possess pathogenic disease resistance and antistress activity in plants as well as high plant growth promoting activity.

BACKGROUND OF THE INVENTION

The compound (2R,3S,24S) -2,3-diacetoxy-22,23-epoxy-24-ethyl-β-homo-7-oxa-5α-cholestan-6-one, having formula 1 of the drawings which is the subject matter of our co-pending Indian Applicaiton No.IP 389/Del/96 is a novel compound useful as an intermediate in the synthesis of homobrassinolide having molecular formula $C_{29}H_{50}O_6$ and isomeric structural formulae 8 and 9 which are highly potent plant growth promoters. The compound of formula 1 is prepared by a process which comprises dihydroxylating (22E, 24S)-24-ethyl-5α-cholestan-2, 22-diene-6-one, having formula 10 of the drawings in a mixture of chlorinated solvents and tert-butanol in presence of tetradecyltrimethylammonium permanganate (TDTAP) reagent at temperature ranging from −5 to 30° C., for one to two hours and separating the resultant compound having structural formula 11 as shown in the accompanying drawings the from the reaction mixture by column chromatography method, acetylating the compound of formula 11 of the drawings to obtain compound of formula 12 of the drawings by slowly adding trifuloroperoxyacetic acid in presence of disodium hydrogen phosphate as a buffer at 0 to 30° C. for a period ranging between 14–18 hours to get compound of the formula 1 of the drawings in 67% yield and the said compound of the formula 1 of the drawings is separated from the reaction mixture by column chromatography. The compound of formula 1 of the drawings when treated with lithium bromide in the presence of a highly acidic sulphonated cation exchange resin and acetonitrile as a solvent, furnishes a compound having molecular formula $C_{33}H_{53}Bro_7$ and isomeric structural formulae 2 and, the compound having molecular formula $C_{33}H_{53}Bro_7$ and structural formulae (2R, 3S, 24S) -2, 3- diacetoxy-22-bromo-24-ethyl-β-homo-7-oxa-22- hydroxy-5α-cholestan-6-one of formula 2 of the drawings and the compound having structural formula (2R, 3S, 24S) -2-3-diacetoxy-23-bromo-24- ethyl-β- homo-7-oxa -22-hydroxy-5α-cholestan -6-one of formula 3 shown in the drawings accompanying this specification, when subject to acetylation, corresponding bromotriacetate having molecular formula $C_{35}$ $E_{55}$ $Bro_8$ is obtained and the bromotriacetate is obtained is further subjected to solvolysis using aqueous acetic acid at elevated temperatures so as to obtain respective hydroxytriacetate having molecular formula $C_{35}H_{56}O_9$ and the structural formulae 4 and 5 as shown in the accompanying drawings. The said compounds of formulae 4 and 5 as shown in the accompanying drawings when subjected to acetylation with acetic anhydride and pyridine give a tetraacetate compound having molecular formula $C_{37}H_{58}O_{10}$ and structural formulae 6 and 7 as shown in the drawings accompanying this specification.

Compounds of formula 6 and formula 7 as shown in the drawings can be separated by column chromatography and after alkaline hydrolysis followed by acidification, produce compounds of formula 8 and formula 9 respectively. Compounds of formula 8 and formula 9 are the structural isomers of homobrassinolide and both the isomers are highly potent plant growth promoters. The compound (2R, 3S, 24S)-2-3, diacetoxy-22,23-epoxy-24-ethyl -β- homo-7- oxa-5 -cholestan-6-one-having formula 1 can be synthesised from stigmasterol.

Although both the compounds of formulae 8 and 9 are potent plant growth promoters, compound 8 is much more active compared to compound 9. Hence, the main objective of the present invention is to develop a convenient process for the preparation of compound having molecular formula $C_{29}H_5O_6$ in high ratio (61:39) of compound of formula 8 to compound of formula 9.

SUMMARY OF THE INVENTION

Accordingly, the present invention relates to a process for the preparation of the said compound of formula 8 in a high ratio as compared to compound of the formula 9, which comprises a sequence of reactions such as epoxide opening, acetylation, solvolysis and again acetylation followed by hydrolysis which affords a suitable method for obtaining a compound having molecular formula $C_{29}H_{50}O_6$ having high ratio (61:39) of compound of formula 8 to compound of formula 9.

In the process of present invention the opening of the epoxide having formula 1 of the drawings, using the reagent lithium bromide in the presence of cation exchange resin and acetonitrile as a solvent, is new, and has not been reported so far.

DETAILED DESCRIPTION OF THE INVENTION

Figure 1A:
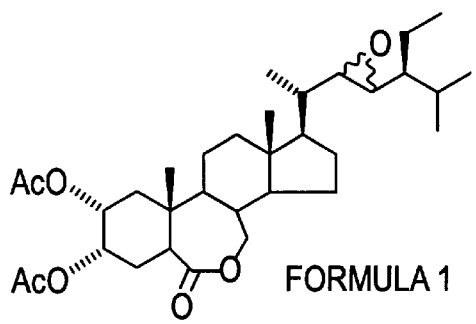
FIGS. 1A to 1L present schematic formulae 1–12, respectively, of reagents, intermediates, and products of the present invention. The drawings are referred to herein as formulae 1–12.
Figure 1B:
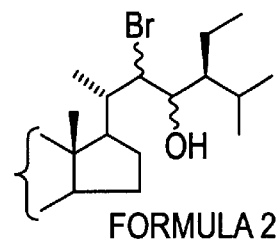
Figure 1C:
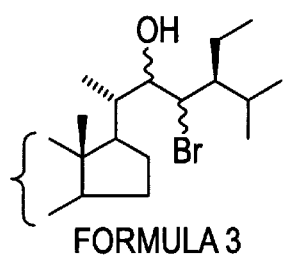
Figure 1D:
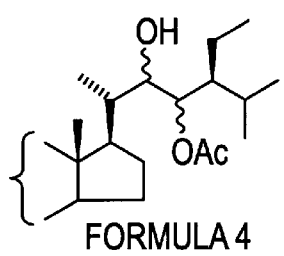
Figure 1E:
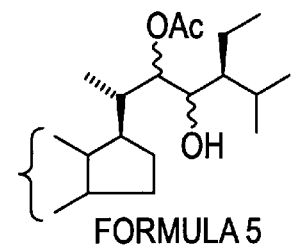
Figure 1F:
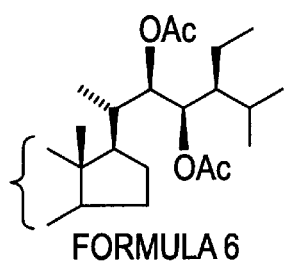
Figure 1G:
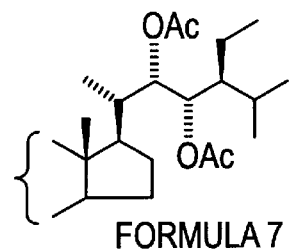
Figure 1H:
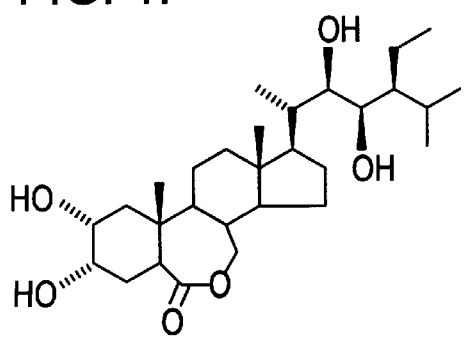
Figure 1I:
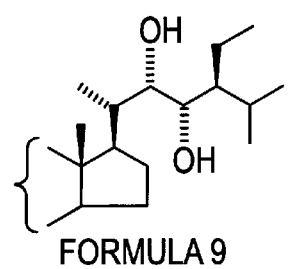
Figure 1J:
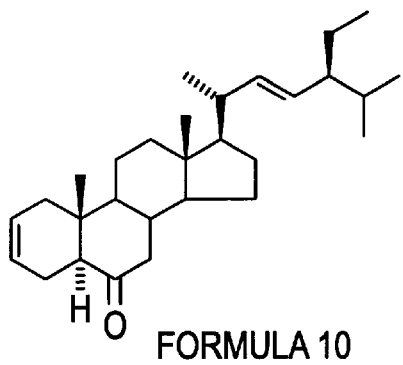
Figure 1K:
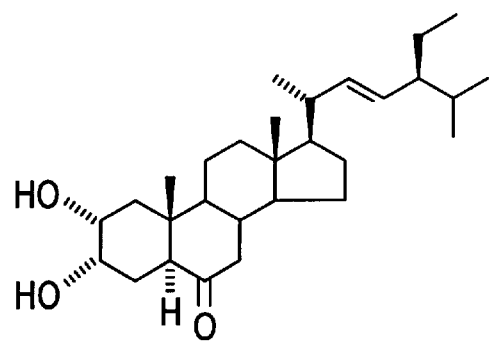
Figure 1L:
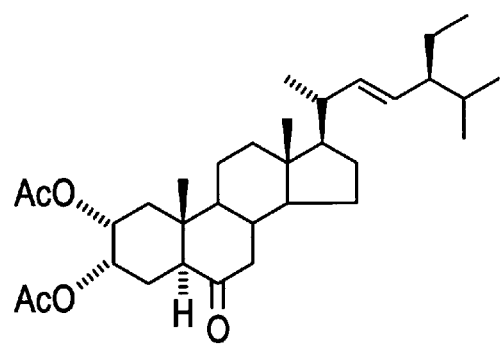

Accordingly, the present invention provides for a compound having molecular formula $C_{29}H_{50}O_6$ and represented by isomeric structural formulae (2R, 3S, 22R, 23R)-2, 3, 22, 23-tetrahydroxy- 24-ethyl-B-homo-7- oxa -5a- cholestan-6-one and (2R, 3S, 22S, 23S)-2,3, 22–23- tetrahydroxy-24-ethyl-β-homo-7-oxa-5α-cholestan-6-one of the following formulae 8 and 9 of the drawings

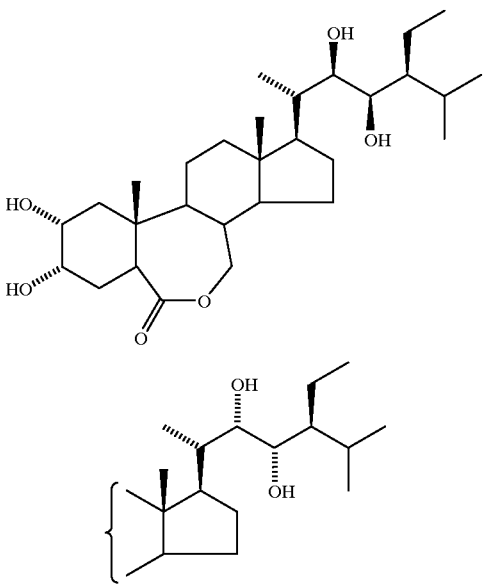

The compounds of formula 8 and 9 are important members of a new class of steroidal phytohormones possessing pathogenic disease resistance and antistress activity in plants as well as high plant growth promoting activity.

The invention further provides a process for the preparation of compound having molecular formula $C_{29}H_{50}O_6$, comprises of following reaction steps:

a. The compound of formula 1 of the drawings when treated with lithium bromide in acetonitrile in presence of cation exchange resin to obtain a compound having molecular formula $C_{33}H_{53}BrO_7$ and isomeric structural formula 2 and 3 of the drawings.

b. Acetylating the compound obtained in step (a) to obtain corresponding bromotriacetate having molecular formula $C_{35}H_{55}BrO_8$. $C_{35}H_{55}BrO_8$ and structural formulae 2 and 3 as shown in the drawings. The said compound of formulae 2 is obtained in the range of 58–66% yeild and the compound of formula 3 is obtained in the range of 29–37% yeild.

c. Subjecting the bromotriacetate obtained in step (b) to solvolysis using 60–90% aqueous acetic acid at elevated temperatures in the range of 75° C. to 90° C. for a period of 14–17 hrs to obtain respective hydroxytriacetate having molecular formula $C_{35}H_{56}O_9$ and structural formulae 4 and 5 of the drawings.

d. Subjecting to acetylation compound of the molecular formula $C_{35}H_6O_9$ obtained in step (c) with acetic anhydride and pyridine in presence of catalytic amount of 4-N,N-dimethylaminopyridine afforded a tetraacetate having molecular formula $C_{37}H_{58}O_{10}$ and isomeric structural formulae 6 and 7 of the drawings.

e. Subjecting compound having molecular formula $C_{37}H_{58}O_{10}$ obtained in step (d) to hydrolysis using potassium carbonate followed by acidification to yield a compound of molecular formula $C_{29}H_{50}O_6$ which on purification afforded compounds having structural formulae 8 and 9 of the drawings in the ratio of 61:39.

Compound having molecular formula $C_{37}H_{58}O_{10}$ and isomeric structural formulae 6 and 7 of the drawings can be separated by column chromatography over silica gel to afford pure compound of formula 6 of the drawings and pure compound of formula 7 of the drawings in the ratio 61:39.

The process of the present invention is described hereinbelow by following examples, which are illustrative only and should not be construed to limit the scope of the present invention in any manner.

EXAMPLE 1

To a solution of (2R,3S,24S)-2,3-diacetoxy-22,23-epoxy-24-ethyl-β-homo-7-oxa-5α-cholestan-6-one of the formula 1 (0.150 g, 0.268 mmol) in dry acetonitrile (20 ml), lithium bromide (0.098 g, 1.13 mmol) and cation exchange resin (150 mg) were added, and the above reaction mixture was stirred at 26° C. for 3 hours. The reaction mixture was then filtered, the filtrate was concentrated, water (20 ml) was added to it and it was extracted with ethyl acetate (3×40 ml). Ethyl acetate extract was washed with water (2×20 ml), sodium bicarbonate (2×20 ml), saturated brine (2×20 ml) and it was dried over $Na_2SO_4$. On evaporation of the solvent, a bromohydrin having molecular formula $C_{33}H_{53}BrO_7$ and isomeric structural formulae 2 and 3 (0.186 g) was obtained, which was purified by column chromatography over silica gel to furnish pure (2R,3S,24S)-2,3-diacetoxy-22-bromo-24-ethyl-β-homo -7-oxa-23-hydroxy-5α-cholestan-6-one of formula 2 (0.100 g, 58%), m.p 204–206° C. (methanol-dichloro methane), followed by (2R,3S,24S)-2,3-diacetoxy-23-bromo-24-ethyl-β-homo-7-oxa-22-hydroxy-5α-cholestan-6-one of formula 3 (0.063 g, 37%), mp 194–197° C. (methanol-dichloro methane).

To a solution of the bromohydrin having molecular formula $C_{33}H_{53}BrO_7$ and isomeric structural formulae (2R,3S,24S)-2,3-diacetoxy-22-bromo-24-ethyl-β-homo-7-oxa-23-hydroxy-5α-cholestan-6-one of formula 2 and (2R,3S,24S)-2,3-diacetoxy-23-bromo-24-ethyl-β-homo-7-oxa-22-hydroxy-5α-cholestan-6-one compound of formula 3 (0.226 g, 0.353 mmol) in dry pyridine (3 ml, 37.i3 mmol) was added acetic anhydride (2 ml, 21.2 mmol) and 4-N,N-dimethylaminopyridine (10 mg, 0.082 mmol). The reaction mixture was stirred at 27° for 26 hours. It was then poured into crushed ice and kept for one hour. Ether extracts (4×30 ml) of this were successively washed with 2N hydrochloric acid (2×30 ml), water (2×20 ml), saturated sodium bicarbonate solution (2×20 ml), water (2×20 ml) and saturated brine (2×20 ml). It was dried over $Na_2SO_4$ and on evaporation of solvent furnished the bromo triacetate as a semisolid compound having molecular formula $C_{35}H_{55}BrO_8$ (0.219 g, 91%).

To this bromotriacetate having molecular formula $C_{35}H_{55}BrO_8$ (0.209 g, 0.320 mmol) in glacial acetic acid (5 ml, 89.9 mmol), water (1.2 ml, 66.6 mmol) was added. The reaction mixture was stirred at 90° C. for a period of 14 hours. It was brought to room temperature and poured into saturated solution of sodium bicarbonate (25 ml), and the mixture was extracted with ethyl acetate (3×30 ml). Ethyl acetate extract was washed with water (3×30 ml) followed by saturated brine (2×20 ml), and it was dried over $Na_2SO_4$. On evaporation of solvent afforded the corresponding hydroxytriacetate, as a semi solid compound having molecular formula $C_{35}H_{56}O_9$ (0.169 g, 85%) and isomeric structural formulae 4 and 5.

To a solution of the above hydroxytriacetate-(0.169 g, 0.273 mmol) having molecular formula $C_{35}H_{56}O_9$ in dry pyridine (3 ml, 37.10 mmol) was added acetic anhydride (2 ml, 21.2 mmol), followed by 4-N, N-dimethylaminopyridine (0.005 g, 0.04 mmol) and the mixture was stirred at 30° C. for 24 hours. The reaction mexture was poured into crushed ice (30 g), kept for one hour, and it was extracted with ether (3×30 ml). The ether extracts were washed successively with water (2×30 ml), dilute hydrochloric acid (2×20 ml), water (2×30 ml), sodium bicarbonate (3×30 ml), water (2×20 ml)

and finally with saturated brine (2×20 ml). The ether extract was dried over $Na_2SO_4$ and on evaporation of solvent gave compound having molecular formula $C_{37}H_{58}O_{10}$ and isomeric structural formulae 6 and 7 (0.176 g 98%).

To a solution of above tetraacetate (0.221 g) having molecular formula $C_{37}H_{58}O_{10}$ in methanol (3 ml), was added a solution of potassium carbonate (1 g, 7.2 mmol) in water (3 ml). This mixture was refluxed for 5 hours, it was cooled and 2N hydrochloric acid (2 ml) was added to it, heated under reflux for one more hour. Methanol was distilled off and the residue was extracted with chloroform (3×30 ml). Chloroform extract was washed with water (3×25 ml), saturated brine (2×25 ml) and it was dried over $Na_2SO_4$. Chloroform was evaporated to afford a compound which on chromatographic purification furnished compound having molecular formula $C_{29}H_{50}O_6$ and isomeric structural formulae 8 and 9 (0.119 g, 68%).

EXAMPLE 2

To a solution of (2R, 3S, 24S)-2,3-diacetoxy-22,23-epoxy-24-ethyl-β-homo-7-oxa-5α-cholestan-6-one of the formula 1 (0.200 g, 0.357 mmol) in dry acetonitrile (22 ml), lithium bromide (0.130 g, 1.49 mmol) and cation exchange resin (200 mg) were added, and the above reaction mixture was stirred at 23° c. for 5 hours. The reaction mixture was then filtered, the filtrate was concentrated, water (20 ml) was added to it and it was extracted with ethyl acetate (3×40 ml). Ethyl acetate extract was washed with water (2×20 ml), sodium bicarbonate (2×20 ml), saturated brine (2×20 ml) and it was dried over $Na_2SO_4$. On evaporation of the solvent, a bromohydrin having molecular formula $C_{33}H_{53}BrO_7$ and isomeric structural formulae 2 and 3 (0.251 g) was obtained, which was purified by column chromatography over silica gel to furnish pure (2R, 3S,24S)-2,3-diacetoxy-22-bromo-24-ethyl-β-homo-7-oxa-23-hydroxy-5α-cholestan-6-one, of the formula 2 (0.139 g, 61%), .m.p. 204–206° (methanol-dichloro methane), followed by (2R,3S,24S)-2,3-diacetoxy-23-bromo-24-ethyl-β-homo-7-oxa-22-hydroxy-5α-cholestan-6-one, of the formula 3 (0.078 g, 34%), mp 194–197° C. (methanol-dichloro methane).

To a solution of bromohydrin having molecular formula $C_{33}H_{53}BrO_7$ and isomeric structural formulae (2R, 3S,24S)-2,3-diacetoxy-22-bromo-24-ethyl-β-homo-7-oxa-23-hydroxy-5α-cholestan-6-one of formula 2 and (2R, 3S,24S)-2,3-diacetoxy-23bromo-24-ethyl-β-homo-7-oxa-22-hydroxy-5α-cholestan-6-one, of formula 3 (0.290 g, 0.452 mmol) in dry pyridine (4 ml, 49.5 mmol) was added acetic anhydride (3 ml, 31.8 mmol) followed by catalytic amount of 4-N, N-dimethylaminopyridine (0.013 g, 0.107 mmol) and the reaction mixture was stirred at 29° c. for 23 hours. The reaction mixture was poured in to crushed ice and kept for one hour. It was then extracted with ether (4×30 ml) and the ether extracts were successively washed with 2N hydrochloric acid (2×30 ml), water (2×20 ml), saturated sodium bicarbonate solution (2×20 ml), water (2×20 ml) and saturated brine (2×20 ml). It was dried over $Na_2SO_4$ and on evaporation of solvent furnished the bromotriacetate having molecular formula $C_{35}H_5BrO_8$ as a semisolid. (0.284 g, 92%). To this bromotriacetate (0.284 g, 0.416 mmol) having molecular formula $C_{35}H_{55}BrO_8$ in glacial acetic acid (7 ml, 126 mmol), water (2 ml, 111 mmol) was added. The reaction mixture was stirred at 75° C. for a period of 16 hours. It was brought to room temperature and poured into saturated solution of sodium bicarbonate (25 ml), and mixture was extracted with ethyl acetate (3×30 ml). Ethyl acetate extract was washed with water (3×30 ml) followed by saturated brine (2×20 ml), and it was dried over $Na_2SO_4$. On evaporation of solvent afforded the corresponding hydroxytriacetate, as a semi solid compound (0.222 g, 86%) having molecular formula $C_{35}H_{56}O_9$.

To a solution of above hydroxytriacetate (0.222 g, 0.358 mmol) having molecular formula $C_{35}H_{56}O_9$ in dry pyridine (4 ml, 49.5 mmol) was added acetic anhydride ( 3 ml, 31.8 mmol) followed by 4-N, N-dimethylaminopyridine (0.010 g, 0.082 mmol) and the mixture was stirred at 27° c. for 26 hours. The reaction mixture was poured into crushed ice (30 g), kept for one hour, and it was extracted with ether (3×30 ml). The ether extracts were washed successively with water (2×30 ml), dilute hydrochloric acid (2×20 ml), sodium bicarbonate (3×30 ml), water (2×20 ml) and finally with saturated brine (2×20 ml). The ether extract was dried over $Na_2SO_4$ and on evaporation of solvent gave a compound having molecular formula $C_{37}H_{58}O_{10}$ and isomeric structural formulae 6 and 7 as semisolid residue (0.231 g, 97.5%).

To a solution of above mixture of tetraacetate (0.280 g) having molecular formula $C_{37}H_{58}O_{10}$ in methanol (3 ml), was added a solution of potassium carbonate (1.3 g, 9.42 mmol) in water (4 ml). This mixture was refluxed for 7 hours, it was cooled and 2N hydrochloric acid (2.5 ml) was added to it, heated under reflux for one more hour. Methanol was distilled off and the residue was extracted with chloroform (3×30 ml). Chloroform extract was washed with water (3×25 ml), saturated brine (2×25 ml) and it was dried over $Na_2SO_4$. Chloroform was evaporated to afford a compound which on chromatographic purification over silica gel furnished compound having molecular formula $C_{29}H_{50}O_6$ and isomeric structural formulae 8 and 9 (0.154 g, 69%).

EXAMPLE 3

To a solution of (2R,3S,24S)-2,3-diacetoxy-22,23-epoxy-24-ethyl-B-homo-7-oxa-5α-cholestan-6-one, of the formula 1 (0.300 g, 0.535 mmol) in dry acetonitrile (25 ml), lithium bromide (0.195 g, 2.2 mmol) and cation exchange resin (300 mg) were added, and the above reaction mixture was stirred at 29° C. for 2 hours. The reaction mixture was then filtered, the filtrate was concentrated, water (20 ml) was added to it and it was extracted with ethyl acetate (3×40 ml). Ethyl acetate extract was washed with water (2×20 ml), sodium bicarbonate (2×20 ml), saturated brine (2×20 ml) and it was dried over $Na_2SO_4$. On evaporation of the solvent, a bromohydrin having molecular formula $C_{33}H_{53}BrO_7$ and isomeric structural formulae 2 and 3 (0.373 g) was obtained, which was purified by column chromatography over silica gel to furnish pure (2R,3S,24S)-2,3-diacetoxy-22-bromo-24-ethyl-β-homo-7-oxa-23-hydroxy-5α-cholestan-6-one, having the formula 2 (0.225 g, 66%), m.p.204–206° C. (methanol-dichloro methane), followed by (2R,3S,24S)-2, 3-diacetoxy-23-bromo-24-ethyl-β-homo-7-oxa-22-hydroxy-5=-cholestan-6-one, having the formula 3 (0.101 g, 29%), mp 194–197° C. (methanol-dichloro methane).

To a solution of bromohydrin having molecular formula $C_{33}H_{53}BrO_7$ and isomeric structural formulae (2R,3S,24S)-2,3-diacetoxy-22-bromo-24-ethyl-β-homo-7-oxa-23-hydroxy-5α-cholestan-6-one, of formula 2 and (2R,3S,24S)-2,3-diacetoxy-23-bromo-24-ethyl-β-homo-7-oxa-22-hydroxy-5α-cholestan-6-one, of formula 3 (0.352 g, 0.549 mmol) in dry pyridine (5 ml, 61.9 mmol) was added acetic anhydride (4 ml, 42.3 mmol), followed by catalytic amount of 4-N,N-dimethylaminopyridine (0.015 g, 0.123 mmol) and the reaction mixture was stirred at 28° C. for 25 hours. The reaction mixture was poured into crushed ice and kept for one hour. It was then extracted with ether (4×30 ml) and the ether extracts were successively washed with 2N hydrochloric acid (2×30 ml), water (2×20 ml), saturated sodium bicarbonate solution (2×20 ml), water (2×20 ml) and saturated brine (2×20 ml). It was dried over $Na_2SO_4$ and on evaporation of solvent finished the bromotriacetate having molecular formula $C_{35}H_{55}BrO_8$ as a semisolid, (0.338 g, 90%).

To this bromotriacetate having molecular formula $C_{33}H_{55}BrO_8$ (0.338 g, 0.495 mmol) in glacial acetic acid (10 ml, 180 mmol), water (3 ml, 167 mmol) was added. The reaction mixture was stirred at 80° C. for a period of 17 hours. It was brought to room temperature and poured into saturated solution of sodium bicarbonate (25 ml), and mixture was extracted with ethyl acetate (3×30 ml). Ethyl acetate extract was washed with water (3×30 ml) followed by saturated brine (2×20 ml), and it was dried over $Na_2SO_4$. On evaporation of solvent afforded the corresponding hydroxy triacetate, as a semisolid compound having molecular formula $C_{35}H_{56}O_9$ and isomeric structural formulae 4 and 5 (0.255 g, 83%).

To a solution of above hydroxytriacetate (0.255 g, 0.411 mmol), having molecular formula $C_{35}H_{56}O_9$ in dry pyridine (5 ml, 61.9 mmol) was added acetic anhydride (4 ml, 42.3 mmol) followed by 4-N, N-dimethylaminopyridine (0.013 g, 0.107 mmol) and the mixture was stirred at 28° C. for 27 hours. The reaction mixture was poured into crushed ice (30 g), kept for one hour, and it was extracted with ether (3×30 ml). The ether extracts were washed successively with water (2×30 ml), dilute hydrochloric acid (2×20 ml), water (2×30 ml), sodium bicarbonate (3×30 ml), water (2×20 ml) and finally with saturated brine (2×20 ml). The ether extract was dried over $Na_2SO_4$ and on evaporation of solvent gave tetraacetate having molecular formula $C_{37}H_{58}O_{10}$ and isomeric struatural formulae 6 and 7 as a semisolid residue (0.267 g, 98%). This was separated by column chromatography over silica gel to get pure (2R,3S,22R,23R) -2,3,22, 23-tetraacetoxy-24-ethyl-β-homo-7-oxa-5α-cholestan-6-one, compound of formula 6 (0.158 g, 61%) mp 137 to 139° c. (ethanol) and (2R,3S,22S,23S)- 2,3,22,23-tetraacetoxy-24-ethyl-β-homo-7-oxa-5α-cholestan-6-one, compound of formula 7 (0.100 g, 39%), mp 185–187° c.

A mixture of compound of formula 6 and formula 7 (0.258 g, 0.39 mmol) in methanol (8 ml), was added a solution of potassium carbonate (2.6 g, 19 mmol) in water (8 ml). This mixture was refluxed for 8 hours, it was cooled and 2 N hydrochloric acid (3 ml) was added to it, heated under reflux for one more hour. Methanol was distilled off and the residue was extracted with chloroform (3×30 ml). Chloroform extract was washed with water (3×25 ml), saturated brine (2×25 ml) and it was dried over $Na_2SO_4$. Chloroform was evaporated to afford compound which on chromatographic purification over silica gel gave compound (0.175 g, 65%) having molecular formula $C_{29}H_{50}O_6$ and isomeric structural formulae 8 and 9.

ADVANTAGES

The advantages of the process of the present invention are:

1. Regioselective conversion of the 22,23-epoxide 1, was carried out with LiBr and highly acidic sulphonated cation exchange resin in acetonitrile to furnish new compound having molecular formula $C_{33}H_3BrO_7$ and isomeric structural formulae 2 and 3 in high yield. Easily available reagent, using which, the reaction goes to completion within a short time.

2. Provides high yields of compound having formula 8 and compound having formula 9 and the process is easy to perform.

3. It gives homobrassinolide having high ratio of compound of formula 8 to compound of formula 9.

We claim:

1. A process for the preparation of steroidal phytohormones possessing pathogenic disease resistance and antistress activity in plants as well as high plant growth promoting activity, from a compound having formula 1 of the drawings, having molecular formula $C_{29}H_{50}O_6$ and represented by isomeric structural formulae (2R,3S,22R,23R)-2, 3,22,23-tetrahydroxy-24-ethyl-β-homo-7-oxa-5α-cholestan-6-one of the following formula

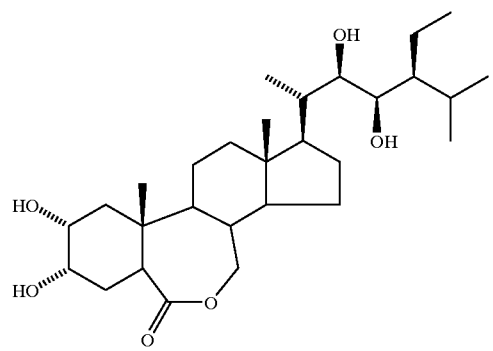

and (2R,3S,22S,23 S)-2,3,22-23-tetrahydroxy-24-ethyl-β-homo-7-oxa-5α-cholestan-6-one of the following formula

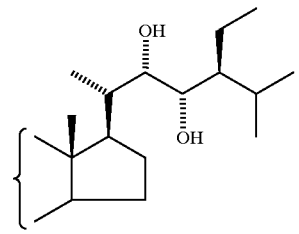

comprising:

a. treating the compound of formula 1 of the drawings with lithium bromide in acetonitrile in the presence of a cation exchange resin to yield compounds having molecular formula $C_{33}H_{53}BrO_7$ and isomeric formulae 2 and 3 of the drawings;

b. acetylating the compounds obtained in (a) to obtain corresponding bromotriacetates having molecular formula $C_{35}H_{53}BrO_8$;

c. subjecting the bromotriacetates obtained in (b) to solvolysis using acetic acid at elevated temperature to obtain respective hydroxytriacetates having molecular formula $C_{35}H_{56}O_9$ and isomeric structural formulae 4 and 5 of the drawings;

d. subjecting to acetylation the compounds of the molecular formula $C_{35}H_{56}O_9$ obtained in (c) with acetic anhydride and pyridine in presence of a catalytic amount of 4-N,N-dimethyl aminopyridine to obtain tetraacetates having molecular formula $C_{37}H_{58}O_{10}$ and isomeric structural formulae 6 and 7 of the drawings;

e. subjecting the compounds having molecular formula $C_{37}H_{58}O_{10}$ obtained in (d) to hydrolysis using potassium carbonate followed by acidification to yield compounds of molecular formula $C_{29}H_{50}O_6$.

2. The process of claim 1 wherein a mixture of compound of the formula 1 of the drawings, lithium bromide and cation exchange resin in acetonitrile is stirred at a temperature ranging from 25 to 30° C. for a period ranging from 2 to 5 hours.

3. The process of claim 1 wherein a compound of the formula 2 of the drawings is obtained in the range of 58–66% yield and compound of the formula 3 of the drawings is obtained in the range of 29–37% yield.

4. The process of claim 1 wherein bromotriacetate having molecular formula $C_{35}H_{55}BrO_8$ is solvolysed using 60 to 90% aqueous acetic acid.

5. The process of claim 1 wherein the solvolysis is conducted in a temperature range of 75° to 90° C.

6. The process of claim 1 wherein the solvolysis is conducted for a period ranging from 14 to 17 hours.

7. The process of claim 1 wherein the compound having structural formula 1 is prepared from stigmasterol.

8. The process of claim 1 wherein purification of the compounds of molecular formula $C_{29}H_{50}O_6$ obtained in (e) results in compounds having structural formulae 8 and 9 in the ratio of 61:39.

* * * * *